(12) United States Patent
Kobayashi et al.

(10) Patent No.: US 9,212,010 B2
(45) Date of Patent: Dec. 15, 2015

(54) CARRIER DEVICE AND CULTURE APPARATUS

(71) Applicant: SANYO ELECTRIC CO., LTD., Osaka (JP)

(72) Inventors: Masahiko Kobayashi, Oizumi-machi (JP); Mikio Houjou, Higashiosaka (JP)

(73) Assignee: PANASONIC INTELLECTUAL PROPERTY MANAGEMENT CO., LTD. (JP)

( * ) Notice: Subject to any disclaimer, the term of this patent is extended or adjusted under 35 U.S.C. 154(b) by 398 days.

(21) Appl. No.: 13/728,108

(22) Filed: Dec. 27, 2012

(65) Prior Publication Data

US 2013/0183751 A1   Jul. 18, 2013

Related U.S. Application Data

(63) Continuation of application No. PCT/JP2011/079764, filed on Dec. 22, 2011.

(30) Foreign Application Priority Data

Feb. 24, 2011   (JP) .................................. 2011-038722

(51) Int. Cl.
| | | |
|---|---|---|
| *C12M 1/34* | (2006.01) | |
| *C12M 3/00* | (2006.01) | |
| *B65G 47/74* | (2006.01) | |
| *C12M 1/00* | (2006.01) | |

(52) U.S. Cl.
CPC ............... *B65G 47/74* (2013.01); *C12M 23/48* (2013.01); *C12M 41/14* (2013.01)

(58) Field of Classification Search
CPC ...... C12M 23/48; C12M 41/14; B65G 47/74; B01L 7/52; B01L 7/00; B01L 2300/0829
USPC ......................................................... 435/287.3
See application file for complete search history.

(56) References Cited

U.S. PATENT DOCUMENTS

| | | | | |
|---|---|---|---|---|
| 5,718,339 | A  * | 2/1998 | Woodruff ................... | 211/41.12 |
| 6,129,428 | A  * | 10/2000 | Helwig et al. ............... | 312/114 |
| 7,137,770 | B2* | 11/2006 | Ueda .............................. | 414/274 |
| 7,395,133 | B2* | 7/2008 | Lowe ............................. | 700/218 |
| 2003/0031602 | A1* | 2/2003 | Weselak et al. ............... | 422/104 |
| 2004/0191925 | A1* | 9/2004 | Seto et al. ..................... | 436/514 |

(Continued)

FOREIGN PATENT DOCUMENTS

| | | |
|---|---|---|
| JP | 3-67806 A | 3/1991 |
| JP | 2006-282332 A | 10/2006 |

(Continued)

OTHER PUBLICATIONS

International Search Report for International Application No. PCT/JP2011/079764, mailed Apr. 17, 2012, with English translation.

*Primary Examiner* — Michael Hobbs
(74) *Attorney, Agent, or Firm* — Cantor Colburn LLP

(57) ABSTRACT

A carrier device may include a loading board, a moving mechanism to move the loading board horizontally for a storage member storing a plurality of containers for storing liquid to be loaded on the loading board; a base material having set thereon the loading board and moving mechanism, and a first mounting member mounted to the base material.

6 Claims, 17 Drawing Sheets

(56) References Cited

U.S. PATENT DOCUMENTS

2004/0256963 A1* 12/2004 Affleck et al. ................ 312/209
2006/0177922 A1* 8/2006 Shamah et al. ............ 435/286.2

FOREIGN PATENT DOCUMENTS

| JP | 4422079 B2 | 12/2009 |
| WO | 2008/108092 A1 | 9/2008 |

* cited by examiner

CARRIER DEVICE AND CULTURE APPARATUS

CROSS-REFERENCE TO RELATED APPLICATION

This application is a continuation under 35 U.S.C. §120 of PCT/JP2011/079764, filed Dec. 22, 2011, which is incorporated herein reference and which claimed priority to Japanese Application No. 2011-038722, filed Feb. 24, 2011. The present application likewise claims priority under 35 U.S.C. §119 to Japanese Application No. 2011-038722, filed Feb. 24, 2011, the entire content of which is also incorporated herein by reference.

DESCRIPTION OF THE RELATED ART

Japanese Patent Publication No. 4422079 discloses a carrier device for carrying a stacker in which a plurality of specimen containers is stored.

For example, when a stacker is installed inside a culture chamber for cultivation of a specimen, it is necessary to bring in the stacker quickly in order to avoid changes in the environmental of the culture chamber. However, the stacker is shaken substantially when carried at high speed and the culture solution held in the container accommodated in the stacker may spill over.

SUMMARY

A carrier device according to at least an embodiment comprises: a loading board; a moving mechanism configured to move the loading board in a horizontal direction so that a storage member configured to store a plurality of containers for storing liquid is loaded on the loading board; a base material configured to have set thereon the loading board and the moving mechanism; a first mounting member mounted to the base material, the first mounting member configured to exert a force to press the storage member against the loading board when the loading board having the storage member loaded thereon is moved to a predetermined position; and a carrier mechanism configured to carry the base material so as to carry the storage member to a target position after the loading board is moved to the predetermined position, wherein the first mounting member pushes a second mounting member mounted on the storage member to press the storage member against the loading board when the loading board having the storage member loaded thereon is moved to a predetermined position.

Other features will become apparent from descriptions of this specification and of the accompanying drawings.

BRIEF DESCRIPTION OF THE DRAWINGS

For more thorough understanding, the following description should be read in conjunction with the accompanying drawings, in which.

DETAILED DESCRIPTION OF THE INVENTION

At least the following details will become apparent from descriptions of this specification and of the accompanying drawings.

Outline of the Incubator 10

Figure 1:
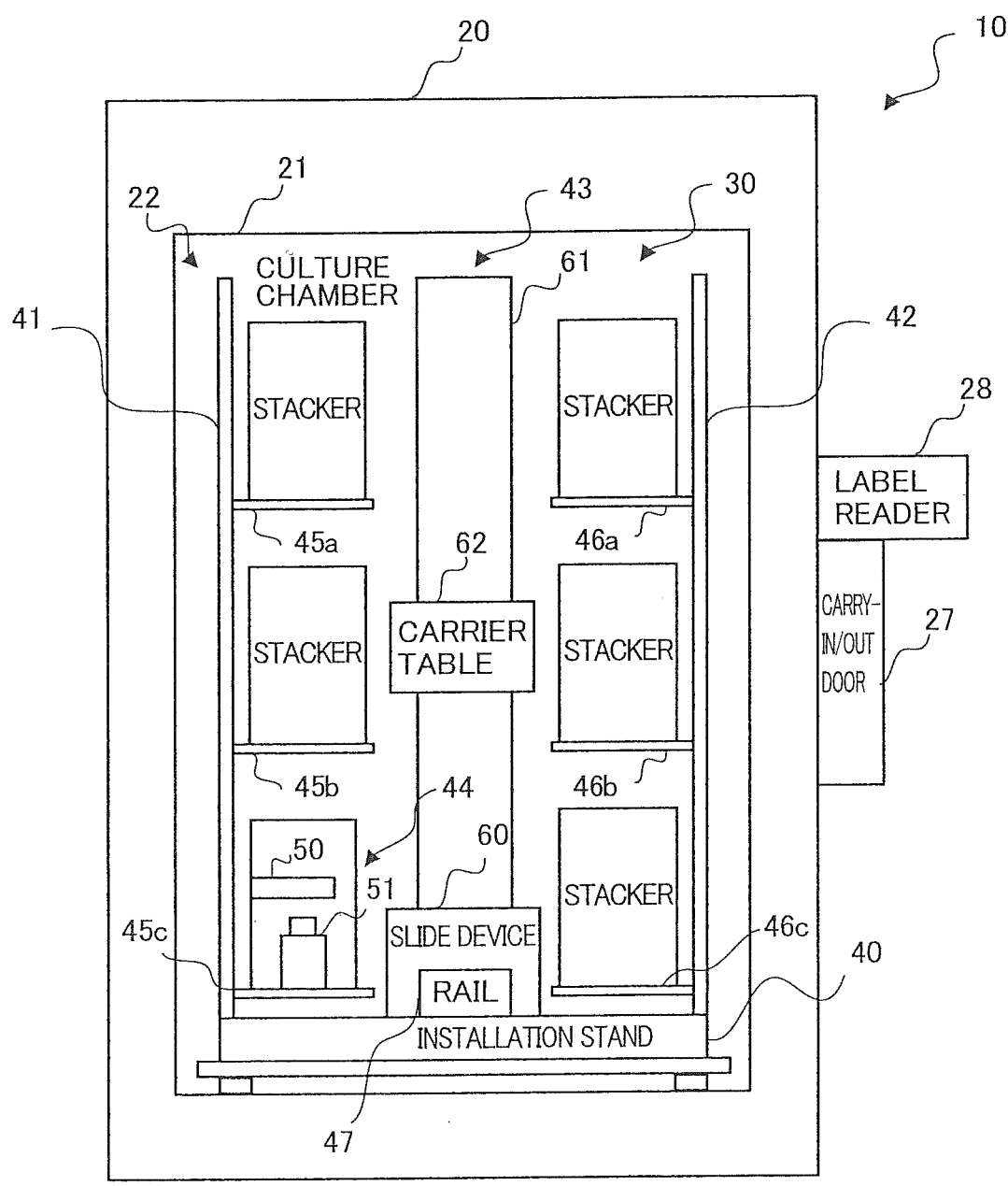
FIG. 1 is a front view of an incubator 10 according to one embodiment.
Figure 2:
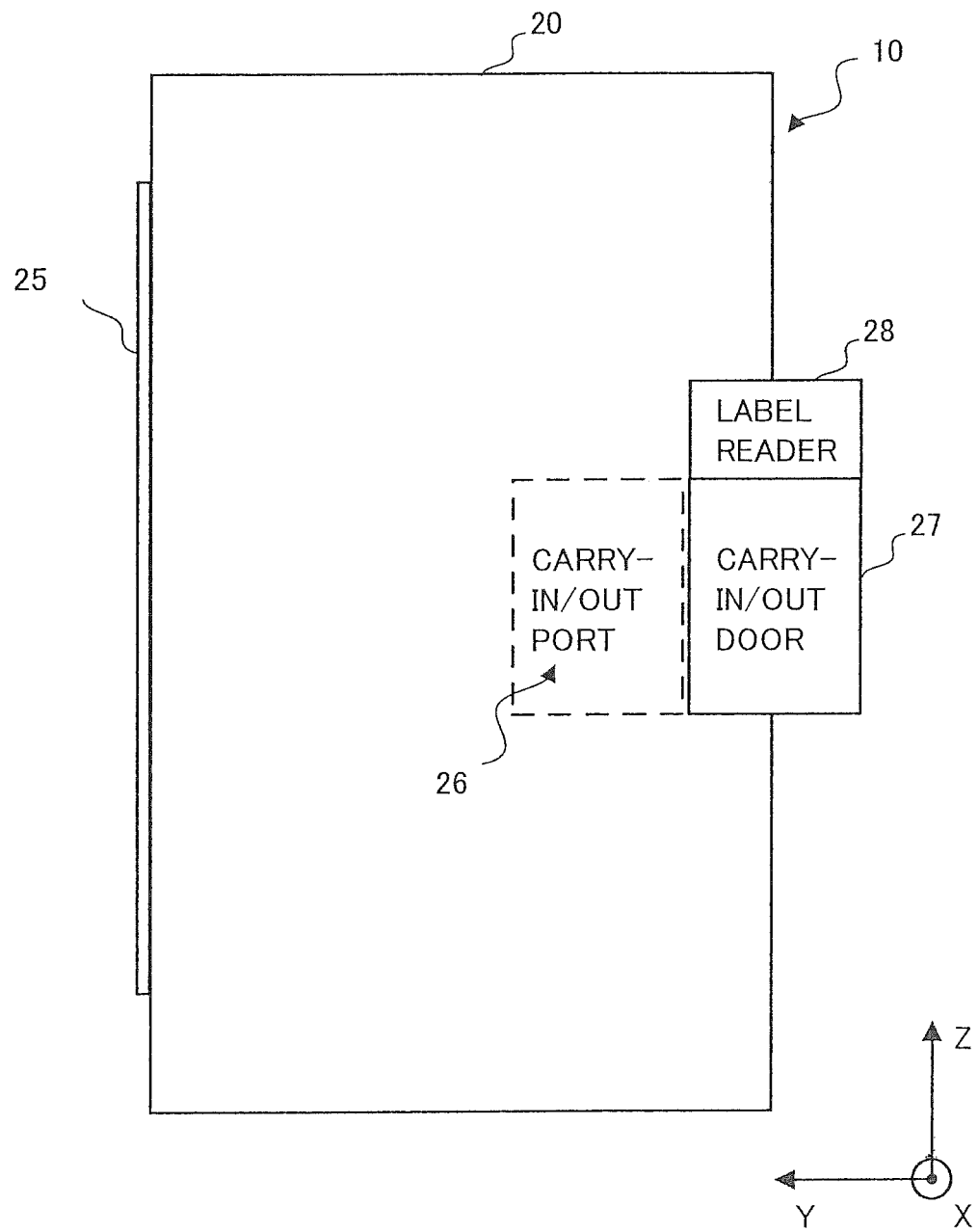
FIG. 2 is a side view of the incubator 10 seen from the positive X direction.
Figure 3:
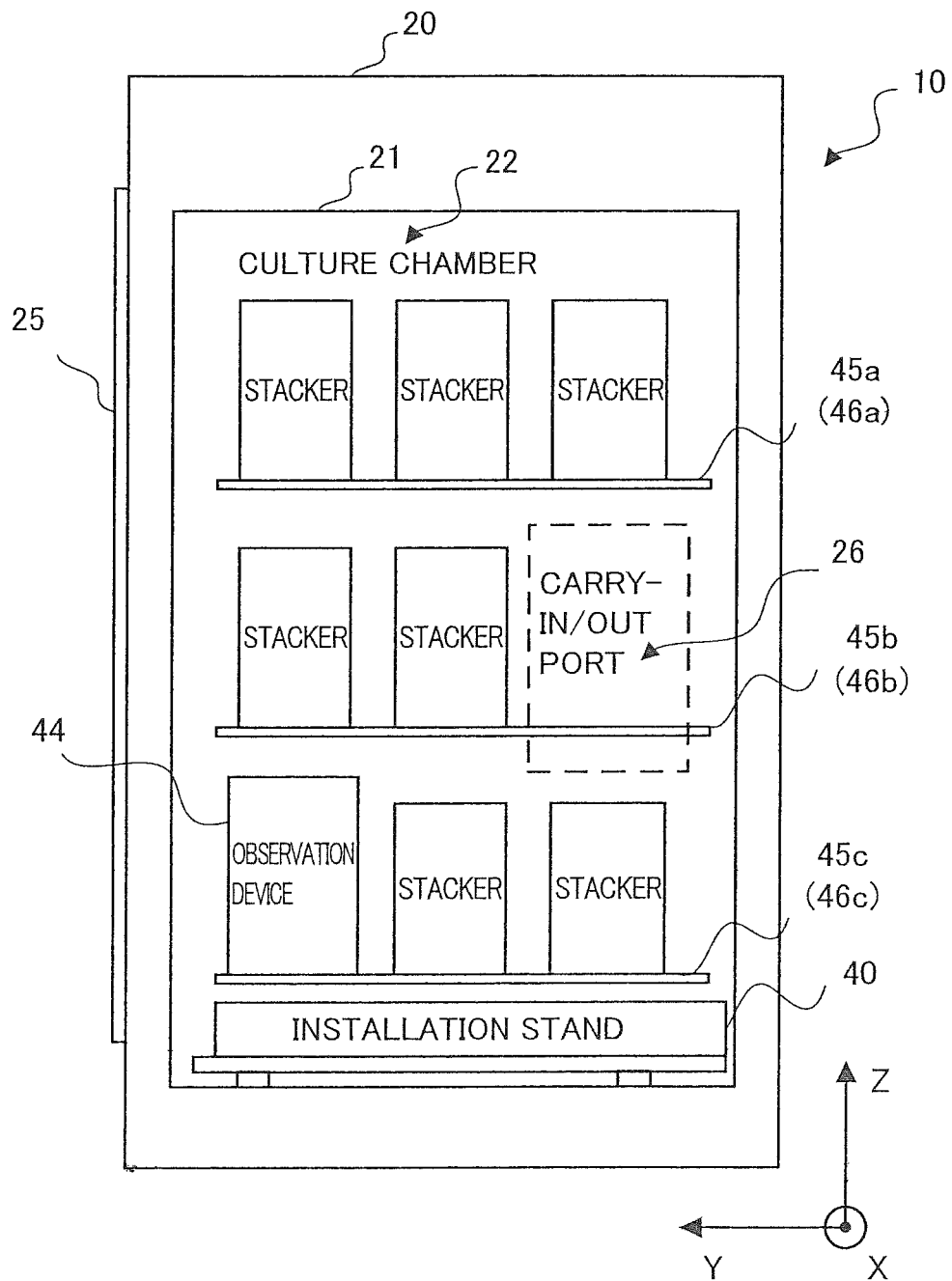
FIG. 3 is a transparent side view for explaining an internal structure of the incubator 10.

The outline of an incubator 10 according to one embodiment will be explained with reference to FIG. 1 to FIG. 3. FIG. 1 is a front view of the incubator 10 in a state with the door on the front side (on the positive Y side) opened and FIG. 2 is a side view of the incubator 10 seen from the positive X direction. FIG. 3 is a transparent side view for explaining the internal structure of the incubator 10. Note that, in the present embodiment, some components constituting the incubator 10 are appropriately omitted from the drawings to ease understanding of the structure of the incubator 10. It is also assumed here that the X-axis direction is the right-left direction with respect to the incubator 10, the Y-axis direction is the front-back direction with respect to the incubator 10 and the Z-axis direction is an up-down direction with respect to the incubator 10.

The incubator 10 (i.e. culture apparatus) is a device for use in cultivating a culture such as cells (or specimens) and microorganisms and is provided with an outer case 20 and an inner case 21.

The outer case 20 is a so-called housing of the incubator 10 and formed into a substantially rectangular parallelepiped shape with an aperture in the front. On the inner side of the outer case 20, the inner case 21 having a shape with an aperture in the front similar to the outer case 20 is arranged so as to be covered by the outer case 20. Also arranged at the front of the outer case 20 is a front door 25 to open and close the aperture of the inner case 21. And, the internal space created in the inner case 21 when the front door 25 is closed serves as the culture chamber 22.

As shown in FIG. 2, a carry-in/out port 26 penetrating the culture chamber 22 from the outside and into the culture chamber 22 is arranged on a right side wall of the incubator 10. The carry-in/out port 26 is an aperture for bringing in therethrough a container storing a culture and a stacker into the culture chamber and also taking them out from the culture chamber. On the right side face of the outer case 20 and in the vicinity of the carry-in/out port 26, a carry-in/out door 27 is mounted so as to open or close the carry-in/out port 26. Then, above the carry-in/out door 27, there is a label reader 28 for reading a label affixed to a culture container when a culture container is brought into or taken out from the culture chamber 22.

As shown in FIG. 1, the inner case 21 is provided with an incubator unit 30 for storing stackers and other components and the incubator unit 30 includes an installation stand 40, storage racks 41 and 42, a carrier device 43 and an observation device 44.

Figure 4:
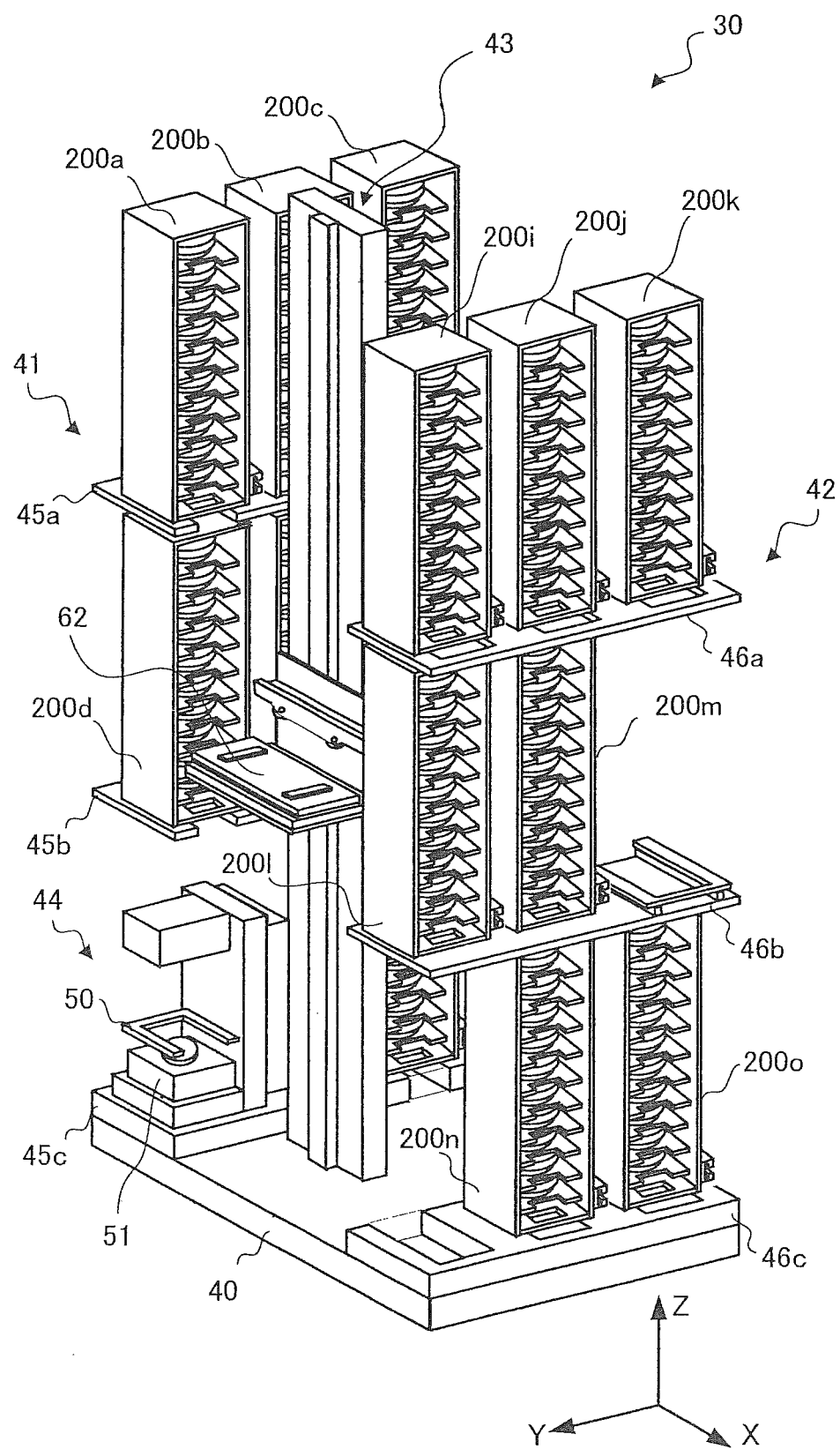
FIG. 4 is a perspective view of an incubator unit 30.

FIG. 4 is a perspective view of the incubator unit 30. The installation stand 40 loaded on the bottom surface of the inner case 21 has installed the storage rack 41 including shelves 45a to 45c, the storage rack 42 including shelves 46a to 46c and the carrier device 43. Note that some of the components constituting the incubator unit 30 are appropriately omitted from FIG. 4 to ease understanding of the relationship among the respective components of the incubator unit 30.

Structure of the Container 100 and the Tray 110

Figure 5:
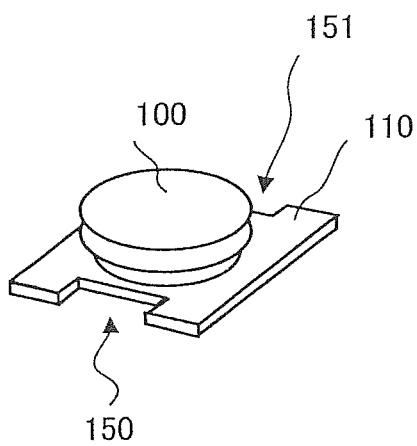
FIG. 5 shows examples of a container 100 and a tray 110.

FIG. 5 illustrates an example of a container 100 for storing a culture (including liquid such as culture solution) and a tray 110 for loading thereon the container 100. The tray 110 is provided with a hole for holding the container 100 and recesses 150 and 151. Note that, as will be described later, the recesses 150 and 151 are used for positioning the tray 110 and restraining the horizontal movement of the tray 110 when the tray 110 is, for example, loaded on the carrier table 62 of the carrier device 43 as shown in FIG. 4.

Structure of the Stacker 200

Figure 6:
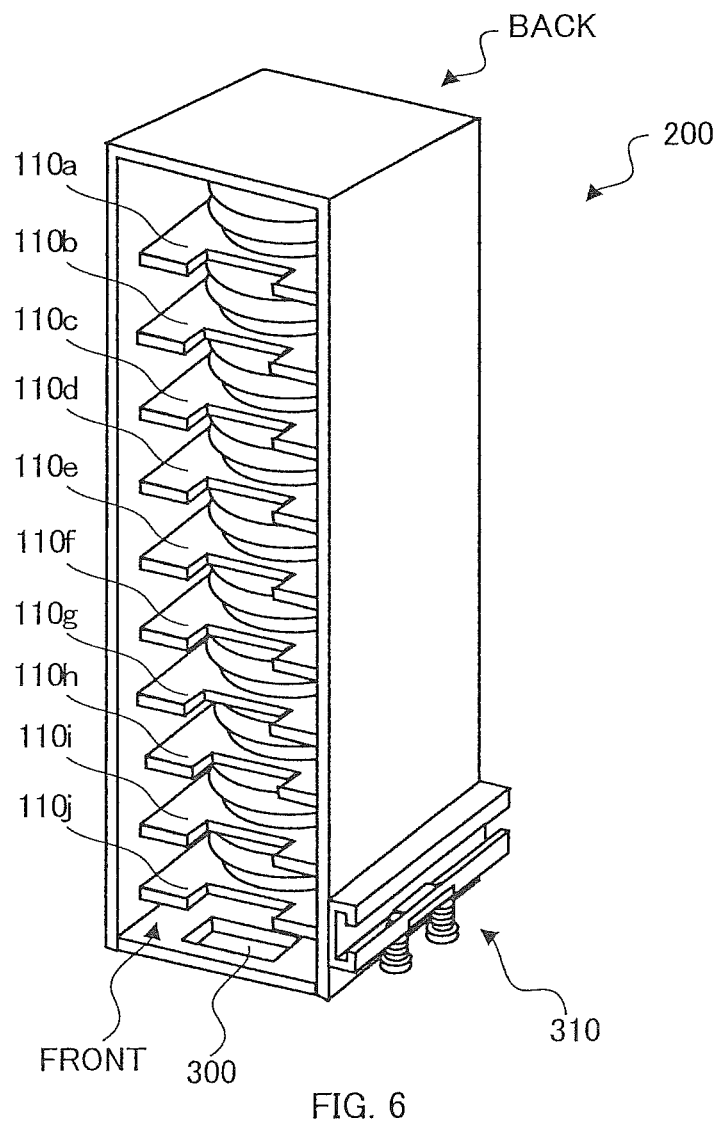
FIG. 6 shows an example of a stacker 200.

FIG. 6 illustrates an example of the stacker 200 (i.e. storage member). The stacker 200 is a case formed into a substantially rectangular parallelepiped shape having apertures at the front and the back. And, the stacker 200 stores, for example, ten trays 110a to 110j in the vertical direction. Two apertures are arranged at the bottom of the stacker 200 (though only aperture 300 is shown in FIG. 6). These apertures are used for positioning the stacker 200 and restraining the horizontal movement of the stacker 200 when the stacker 200 is loaded on the carrier table 62. A guide receiving mechanism 310 is also mounted on a side face of the stacker 200.

Figure 7:
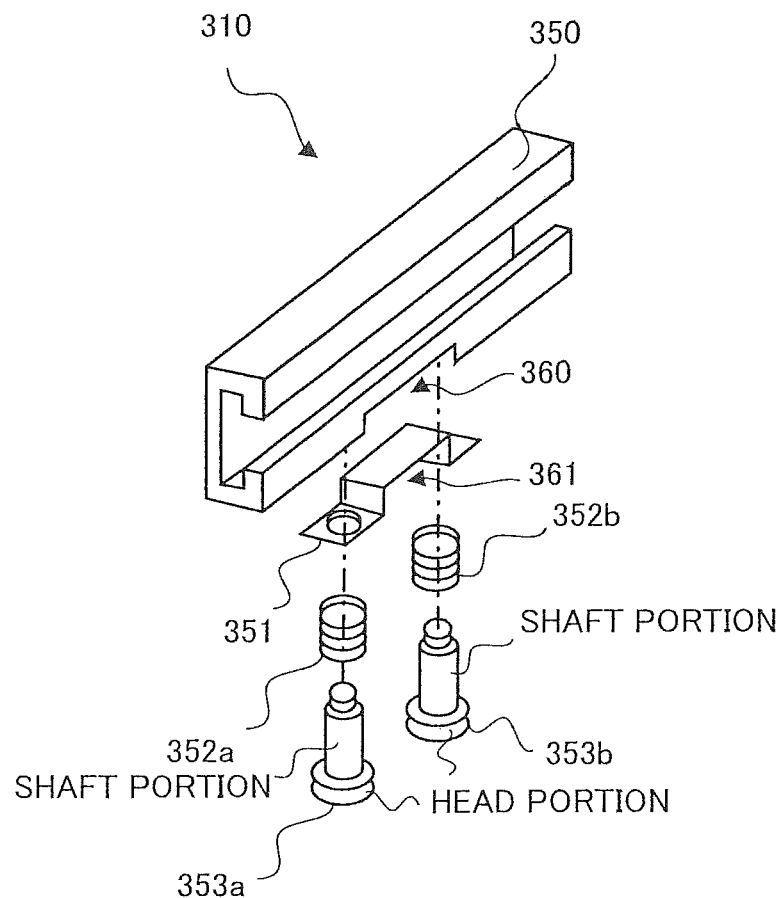
FIG. 7 is an exploded perspective view of a guide receiving mechanism 310.

The guide receiving mechanism 310 (second mounting member) is a member to exert elastic force on the stacker 200 so that the stacker 200 loaded on the carrier table 62 is pushed against the carrier table 62. FIG. 7 is an exploded perspective view of the guide receiving mechanism 310. The guide receiving mechanism 310 includes a guide rail 350, a bulged member 351, springs 352a and 352b and bolts 353a and 353b.

The guide rail 350 is a rail to guide the guide mechanism mounted on the carrier table 62 to be described later. An aperture 360 is arranged in the vicinity of the center on the bottom side of the guide rail 350.

The bulged member 351 is, for example, a plate formed into a raised shape. The bulged part 361 of the bulged member 351 is inserted into the aperture 360 of the guide rail 350 from the bottom side. And, the bulged member 351 is mounted on the guide rail 350 by the bolt 353a whose shaft portion is inserted into the spring 352a and the bolt 353b whose shaft portion is inserted into the spring 352b. As a result, when the bulged part 361 of the bulged member 351 is pressed from above, the springs 352a and 352b are contracted. Then, a downward force is applied to the guide rail 350 by an elastic force of the contracted springs 352a and 352b, which results in application of a downward force to the stacker 200 on which the guide rail 350 is mounted. Therefore, for example, when the bulged member 351 is pressed from above and the springs 352a and 352b are contracted when the stacker 200 is loaded on the carrier table 62, the stacker 200 is pressed onto the carrier table 62.

The storage rack 41 shown in FIG. 1 and FIG. 4 is a rack for use in storing the observation device 44 and a plurality of stackers, and is mounted on the installation stand 40 so that the storage rack 41 is arranged near the left side wall of the inner case 21. The storage rack 41 also includes three shelves 45a to 45c mounted in the vertical direction (or the Z-axis direction).

Figure 8:
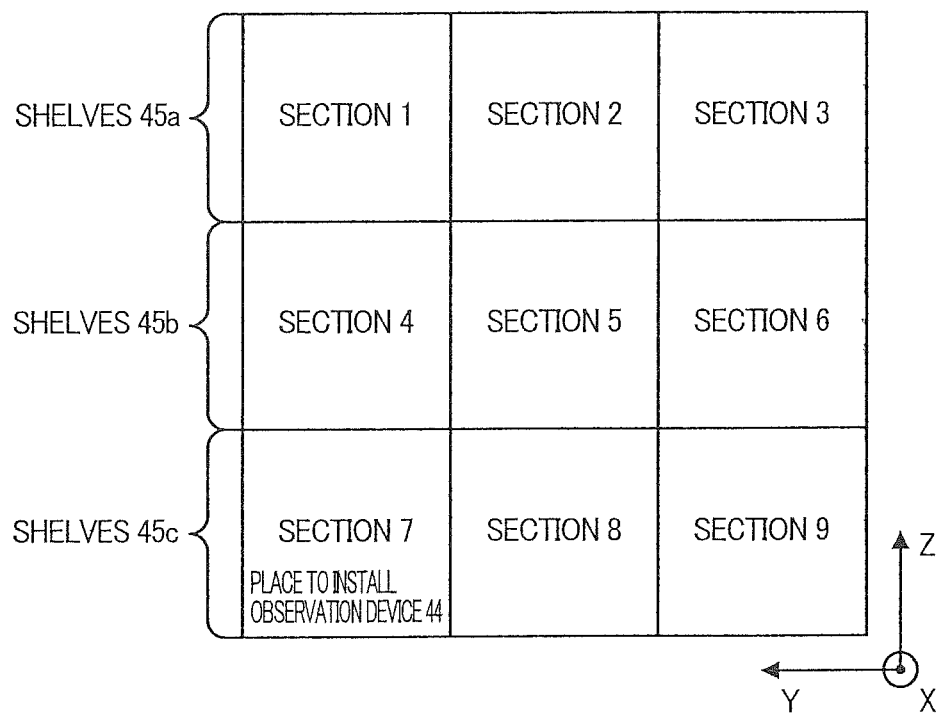
FIG. 8 illustrates sections in a storage space of a storage rack 41.

In the present embodiment, a storage space of the storage rack 41 is divided into nine virtual sections including sections 1 through 9 as shown in FIG. 8. Each of the sections has a capacity to store a stacker and the observation device 44. It is assumed that three sections including the sections 1 through 3 are allocated to a storage space of the shelf 45a, three sections including the sections 4 through 6 are allocated to a storage space of the shelf 45b, and three sections including the sections 7 through 9 are allocated to a storage space of the shelf 45c. It is also assumed that the section 7 facing the front door 25 of the shelf 45c is a section in which the observation device 44 is installed. Therefore, in the storage space of the storage rack 41, sections enabling installation of the stackers are sections 1 to 6, 8 and 9.

The storage rack 42 is a rack for storing a plurality of stackers similar to the storage rack 41 and is mounted on the installation stand 40 so that the storage rack 42 is arranged near the right side wall of the inner case 21. The storage rack 42 also includes three shelves 46a to 46c mounted in the vertical direction. Note that the height of at which the column plates 45a to 45c are mounted are the same as those at which shelves 46a to 46c are mounted.

Figure 9:
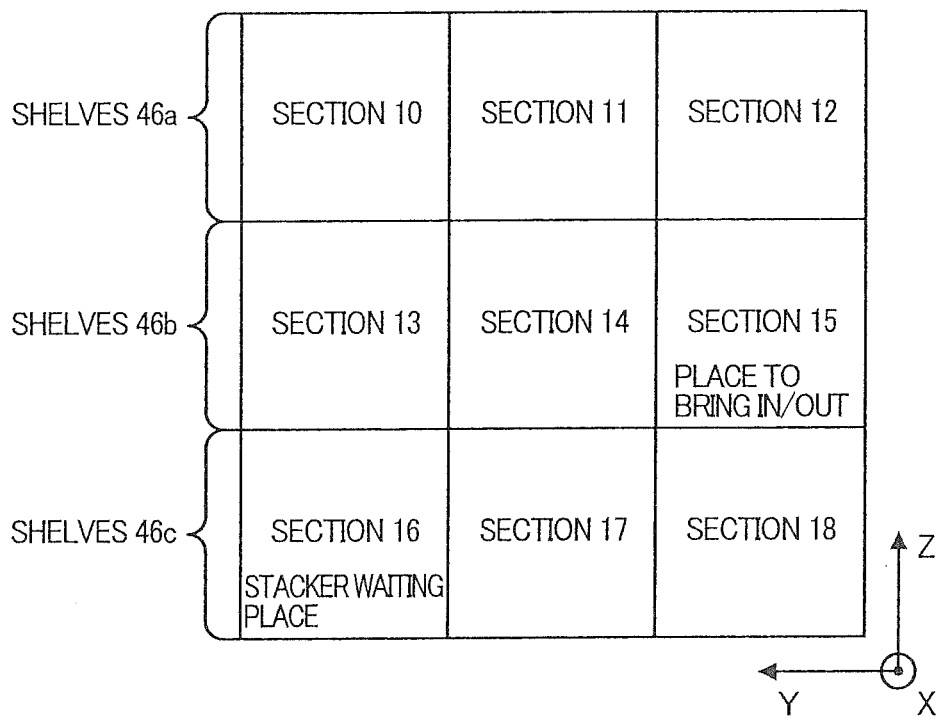
FIG. 9 illustrates sections in a storage space of a storage rack 42.

The storage space of the storage rack 42 is also divided into nine virtual sections including sections 10 through 18 as shown in FIG. 9 in the same manner as the storage rack 41. It is assumed that three sections including sections 10 through 12 are allocated to the storage space of the shelf 46a, three sections including sections 13 through 15 are allocated to the storage space of the shelf 46b and three sections including sections 16 through 18 are allocated to the storage space of the shelf 46c. It is also assumed that section 15 which opposes the carry-in/out port 26 for bringing in or taking out a stacker and located closest to the carry-in/out port 26 is a section in which installation of a stacker is not allowed. It is further assumed that section 16 opposing section 7 for arranging the observation device 44 is a section where a stacker waits for being observed by the observation device 44. Therefore, in the storage space of the storage rack 42, sections enabling installation of the stackers are sections 10 to 14, 17 and 18. Also, by setting section 16 opposing section 7 as the stacker for observation waiting section, for example, the distance along which the container stored in the stacker in section 16 is carried to the observation device 44 by the carrier device can be shortened.

Note that arrangement of the shelves in each of the storage racks 41 and 42 is not limited to three stages and may also be in a single stage. In such case, the installation stand 40 may also serve as a shelf.

The carrier device 43 shown in FIG. 1 is a device to carry the container 100 and the stacker 200. The carrier device 43 whose details will be described later is movably mounted on the rail 47 which is mounted on the surface of the installation stand 40 along the Y-axis direction. Note that the rail 47 is mounted in a position between the storage rack 41 and the storage rack 42.

The observation device 44 is a device to observe a culture stored in the container 100 and is configured to include an observation stand 50 and a camera 51. The container 100 carried by the carrier device 43 is loaded onto the observation stand 50. The observation stand 50 also has a motor to move the observation stand 50 in respective directions of X-axis, Y-axis and Z-axis so that an image of the container 100 can be easily taken by the camera 51. The camera 51 takes a picture and an image of the culture held in the container 100.

Details of the Carrier Device 43

Figure 10:
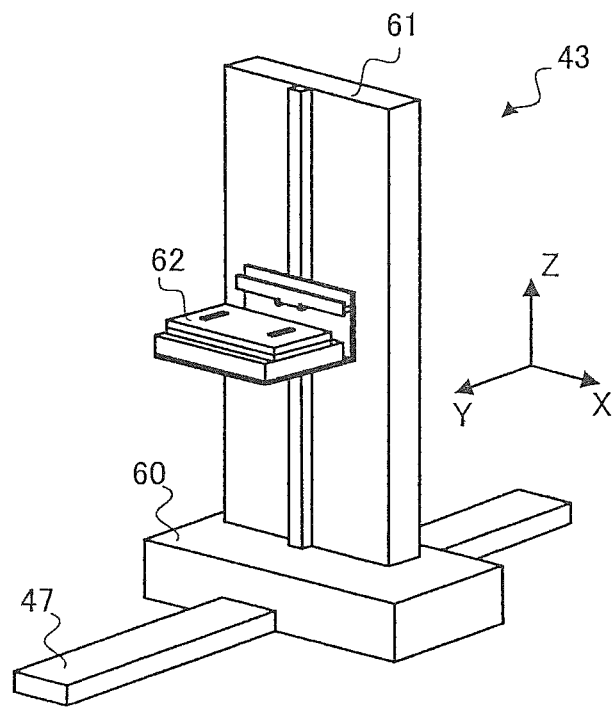
FIG. 10 is a perspective view of a carrier device 43.

Here, details of the carrier device 43 will be explained. As shown in FIG. 10, the carrier device 43 is configured to include a slide device 60, a rail member 61 and the carrier table 62. Note that FIG. 10 is a perspective view of the carrier device 43.

The slide device 60 is movably mounted on the rail 47 extending along the Y-axis direction. Then, the slide device 60 is allowed to move (or slide) along the rail 47 by rotation of an internally provided motor (for the Y-axis). The rail member 61 is also mounted on the slide device 60 along the vertical direction. The carrier table 62 is movably mounted on the rail member 61 along the Z-axis direction. Then, the carrier table 62 is allowed to move (or slide) in the Z-axis direction by rotation of a motor (for the Z-axis) provided internal to the slide device 60. Therefore, the slide device 60 and the carrier table 62 function as a carrier mechanism.

Figure 11:
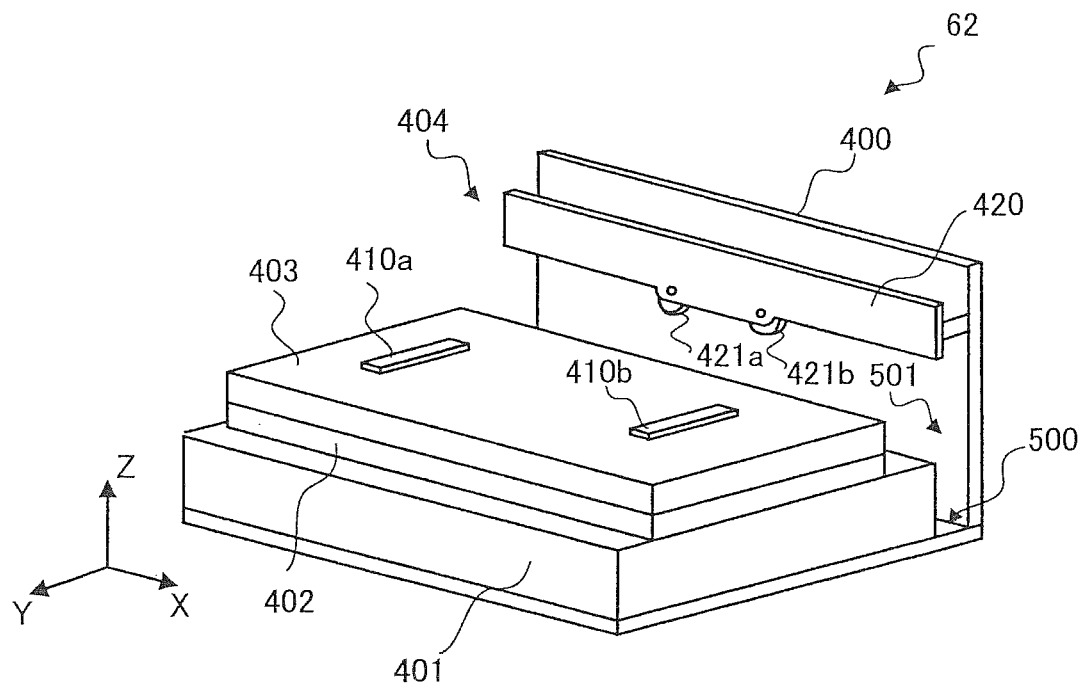
FIG. 11 is a perspective view of a carrier table 62.
Figure 12:
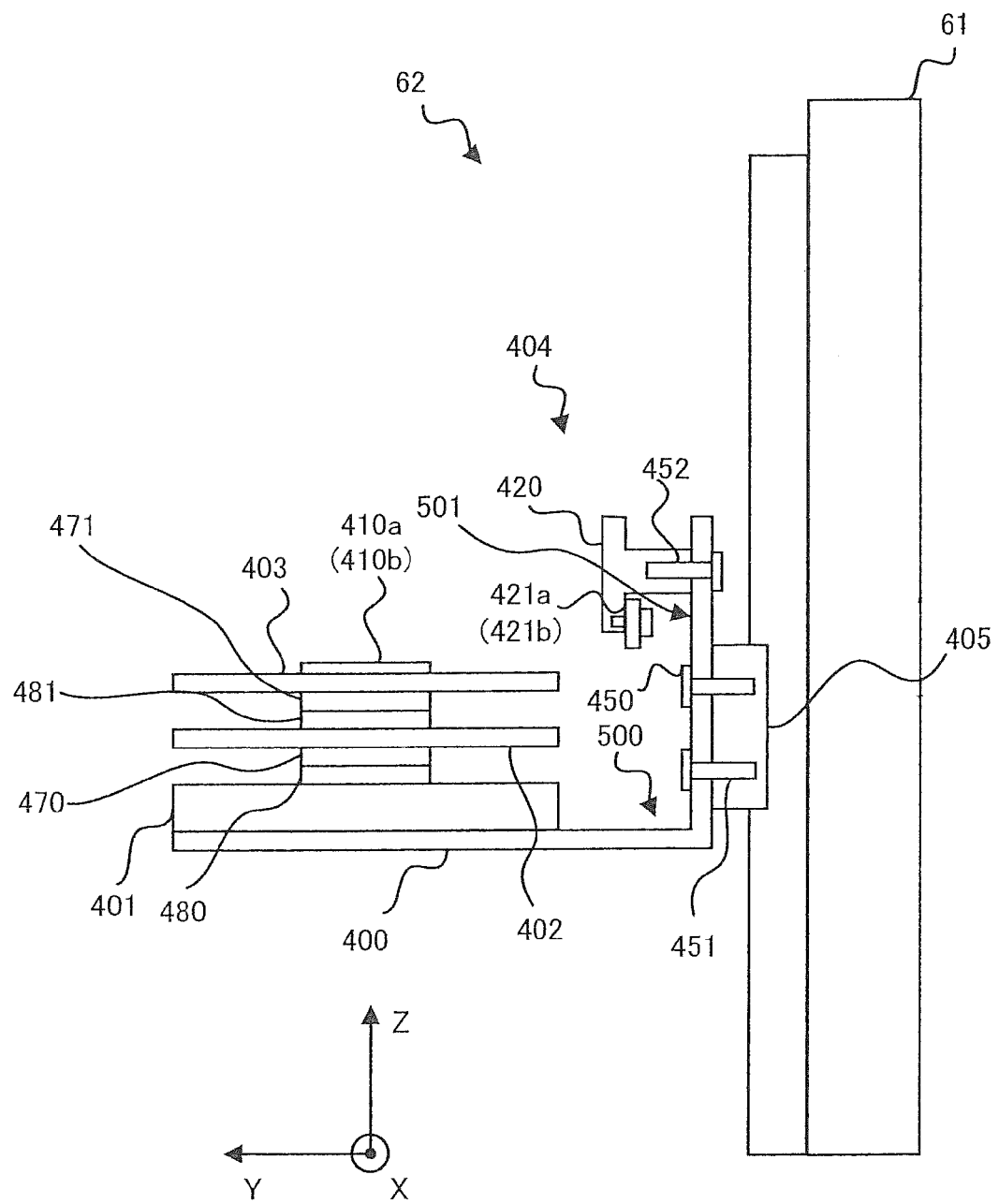
FIG. 12 is a transparent side view of the carrier table 62 seen from the positive X-axis direction.

FIG. 11 is a perspective view of the carrier table 62 and FIG. 12 is a transparent side view of the carrier table 62 to be seen from the positive X-axis direction. Note that some components are omitted from FIG. 11 for the sake of convenience. In addition, even though slide plates 402 and 403 and other components are drawn in close contact with each other in FIG. 11 for the sake of convenience, each of the plates is actually arranged with a gap interposed therebetween so that each of the plates is allowed to slide.

The carrier table 62 includes a base plate 400, a stand 401, the slide plates 402 and 403, a guide mechanism 404 and a slider 405. Note that the base plate 400 and the stand 401 correspond to the base material.

The base plate 400 is a plate which is bent and formed into an L shape and mounted on the slider 405 by bolts 450 and 451 so that the plane 500 of the base plate 400 becomes horizontal. Note that the slider 405 is movably mounted on the aforementioned rail member 61 in the Z-axis direction and is allowed to move (or slide) in the Z-axis direction by rotation of a motor (for the Z-axis) which is provided internal to the slide device 60. The stand 401 is also mounted on the plane 500 of the base plate 400 and a rail 470 extending in the X-axis direction is mounted on the surface of the stand 401.

The slider 480 mounted on the bottom face of the slide plate 402 is movably mounted on the rail 470 of the stand 401. Therefore, the slide plate 402 is allowed to move (or slide) on the stand 401 by rotation of a motor (for the X axis) provided internal to the slide device 60. A rail 471 extending in the X-axis direction is also mounted on the surface of the slide plate 402.

The tray 110 or the stacker 200 is selectively loaded on the slide plate 403 (loading board). The slider 481 mounted on the bottom face of the slide plate 403 is also movably mounted on the rail 471. Therefore, the slide plate 403 is allowed to move (or slide) on the slide plate 402 by rotation of a motor (for the X-axis) provided internal to the slide device 60.

Therefore, for example, the slide plates 402 and 403 function as a slide mechanism (or moving mechanism). The stacker 200 loaded on the slide plate 403 is also moved in the X-axis direction by sliding of the two slide plates 402 and 403. The slide plate 403 is further allowed to move in the X-axis direction in a distance sufficient enough for a user to load the stacker 200 onto the slide plate 403 outside the culture chamber 22. Also, when the slide plate 403 is moved outside the culture chamber 22 or when the slide plate 403 is moved inside the culture chamber 22, the slide plate 403 passes through the aforementioned section 15 and the carry-in/out port 26.

Figure 13:
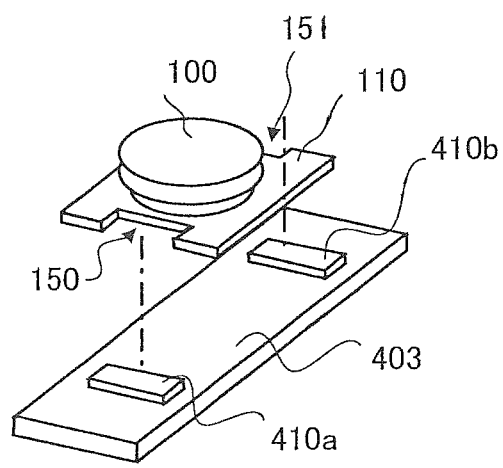
FIG. 13 illustrates a relationship between the tray 110 and a slide plate 403.
Figure 14:
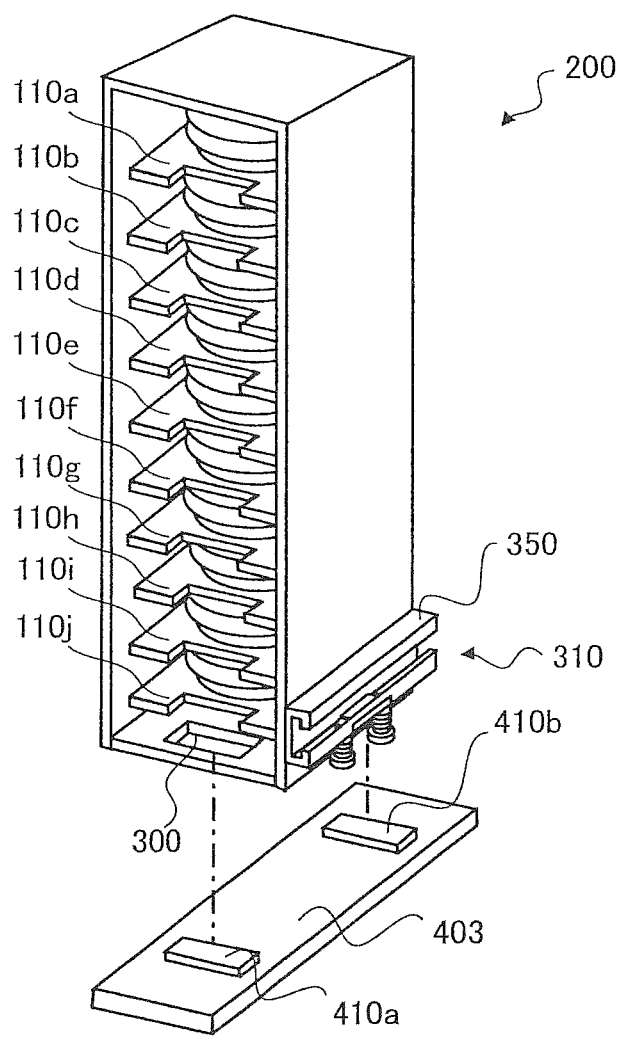
FIG. 14 illustrates a relationship between the stacker 200 and the slide plate 403.

Protruding parts 410a and 410b are formed on the surface of the slide plate 403. When the tray 110 is loaded on the slide plate 403, the recess 150 of the tray 110 fits into the protruding part 410a and the recess 151 fits into the protruding part 410b as shown in FIG. 13. In contrast, as shown in FIG. 14, when the stacker 200 is loaded onto the slide plate 403, the protruding part 410a fits into the aperture 300 at the bottom of the stacker 200 and the protruding part 410b fits into an aperture not shown at the bottom of the stacker 200. As a result, when the tray 110 or the stacker 200 is loaded onto the slide plate 403, movement thereof in the horizontal direction is restricted. Thus the slide plate 403 has a shape that determines the position of the tray 110 or the stacker 200 and restricts the movement thereof in the horizontal direction.

The guide mechanism 404 (i.e. first mounting member) shown in FIG. 11 and FIG. 12 is also a member that presses the stacker 200 loaded on the slide plate 403 against the slide plate 403 together with the guide receiving mechanism 310 arranged on the stacker 200 side. The guide mechanism 404 includes a guide member 420 and guide rollers 421a and 421b.

The guide rollers 421a and 421b are mounted in the vicinity of the center of the guide member 420. The guide member 420 is also mounted on a face 501 of the base plate 400 by a bolt 452 so that the guide member 420 and the guide rollers 421a and 421b are guided by the guide rail 350 arranged on the stacker 200 side when the slide plate 403 on which the stacker 200 is loaded slides. That is, the guide member 420 is mounted in a position to allow the guide rollers 421a and 421b roll along the guide rail 350 when the slide plate 403 slides.

Operation of the Guide Receiving Mechanism 310 and the Guide Mechanism 404

Figure 15:
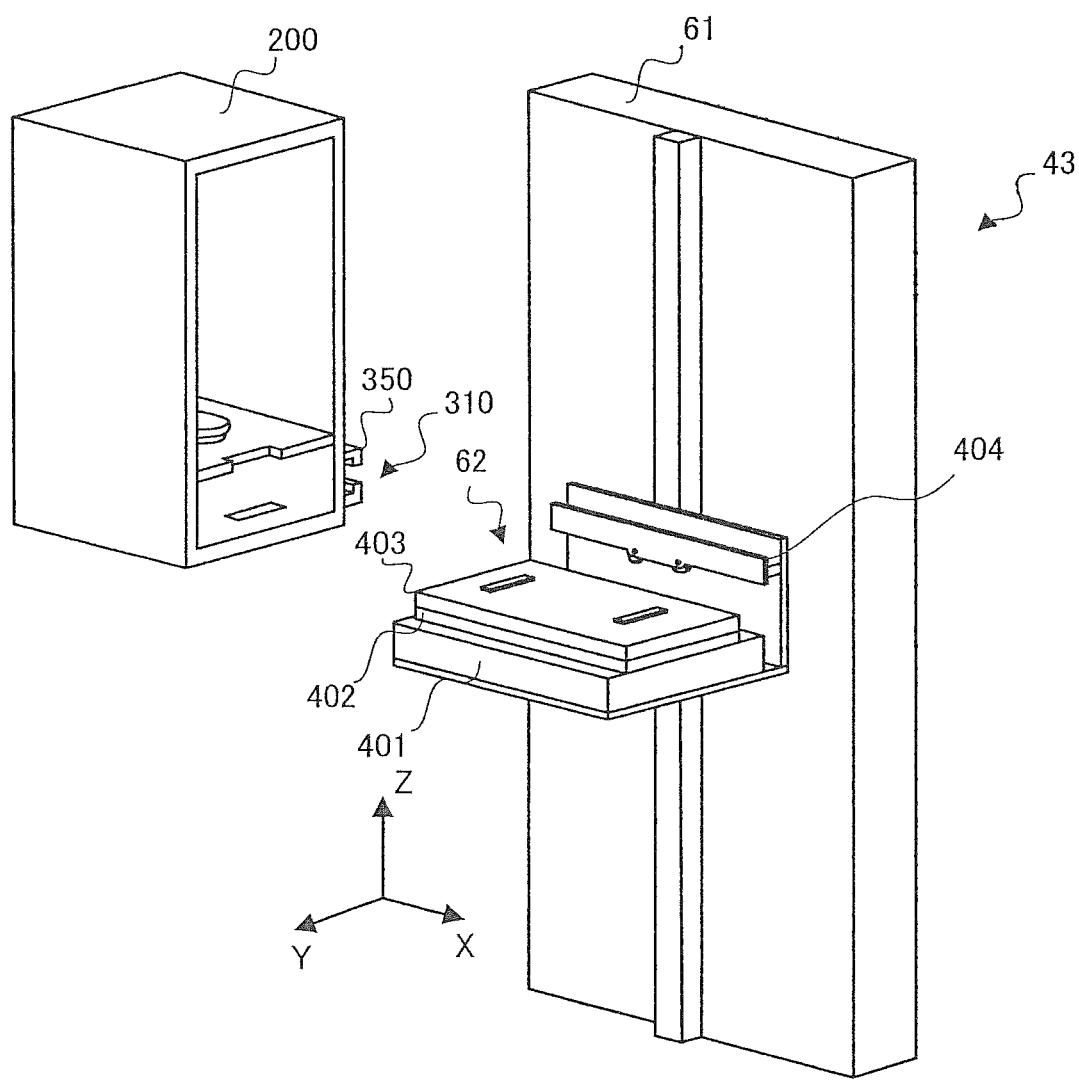
FIG. 15 is a perspective view illustrating a state observed before the stacker 200 is loaded onto the carrier table 62.

Here, the way in which the guide receiving mechanism 310 arranged on the stacker 200 side and the guide mechanism 404 arranged on the carrier table 62 side operate will be explained with reference to FIG. 15 and FIG. 16. FIG. 15 is a perspective view illustrating a state observed before the stacker 200 is loaded onto the carrier table 62 and FIG. 16 is a schematic diagram for explaining how the guide receiving mechanism 310 and the guide mechanism 404 operate. Note that only the principal components are illustrated in FIGS. 15 and 16 for the sake of convenience.

Firstly, the carrier device 43 causes movement of the slide plates 402 and 403 to move in a horizontal direction in a state shown in FIG. 15 so that that the stacker 200 which is stored is loaded onto the slide plate 403 of the carrier table 62. Specifically, the slide plates 402 and 403 are made to slide to the negative X direction from a state in which the slide plates 402 and 403 has not been slid at all or in other words a state as shown in FIG. 15 in which the slide plates 402 and 403 are completely stored (hereinafter, the position of the slide plates in this state is referred to as a predetermined position A).

Figure 16A:
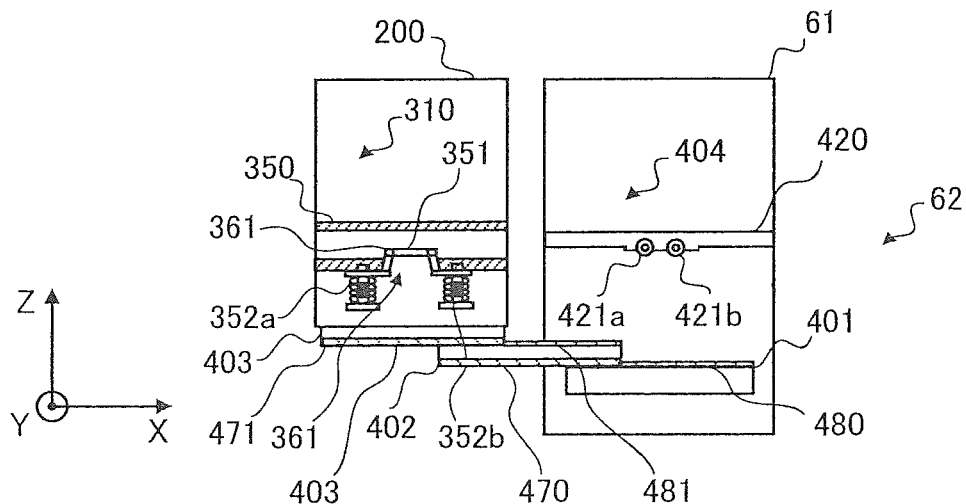
FIGS. 16A, 16B and 16C are a schematic diagram for explaining how the guide receiving mechanism 310 and a guide mechanism 404 operate.

Then, when the stacker 200 is loaded onto the slide plate 403 as shown in FIG. 16A, the carrier device 43 causes the slide plates 402 and 403 to slide (i.e., to be stored) in the positive X direction so that the guide member 420 is guided along the guide rail 350. Specifically, the slider 470 on the bottom surface of the slide plate 402 slides on the rail 480 mounted on the stand 401. The slider 471 on the bottom surface of the slide plate 403 slides on the rail 481 mounted on the slide plate 402. Note that the slider 405 and other components are omitted in the following explanation for the sake of convenience.

Figure 16B:
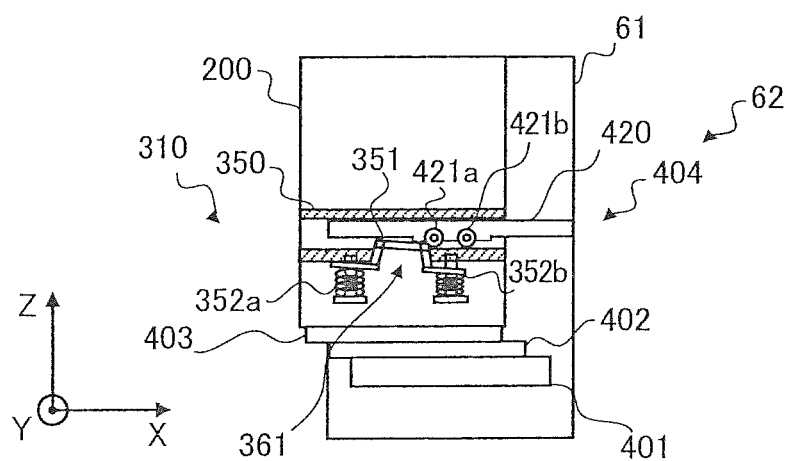

When the slide plates 402 and 403 are made to slide in the positive X direction, the guide member 420 enters into the guide rail 350 and the guide roller 421a rolls along the guide rail 350 to eventually ride on the bulged part 361 of the bulged member 351 to start pressing it downward as shown in FIG. 16B. As a result, the bulged member 351 sinks down so that the spring 352b is gradually contracted.

Figure 16C:
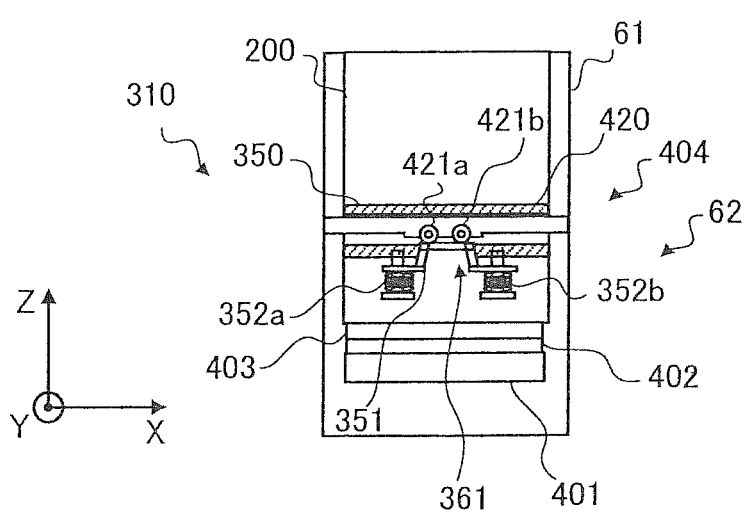

Thereafter, when the slide plates 402 and 403 further slide to the positive X direction to be stored as shown in FIG. 16C, the guide roller 421b also rolls and rides on the bulged part 361 to press thereagainst. As a result, the springs 352a and 352b are both contracted and an elastic force is exerted via the bolts 353a and 353b and on the guide rail 350 to receive a downward force. In this way, the stacker 200 is pressed onto the slide plate 403.

Note that, in the present embodiment, the guide receiving mechanism 310 and the guide mechanism 404 are assumed to be designed so that, for example, both of the guide rollers 421a and 421b ride on the bulged part 361 to press thereagainst while the slide plates 402 and 403 are in a state stored in the predetermined position A. Therefore, when the slide plate 403 is moved to the predetermined position A, the stacker 200 is certainly pressed onto the slide plate 403.

Outline of the Controller 15 for Controlling Operation of the Incubator 10

Figure 17:
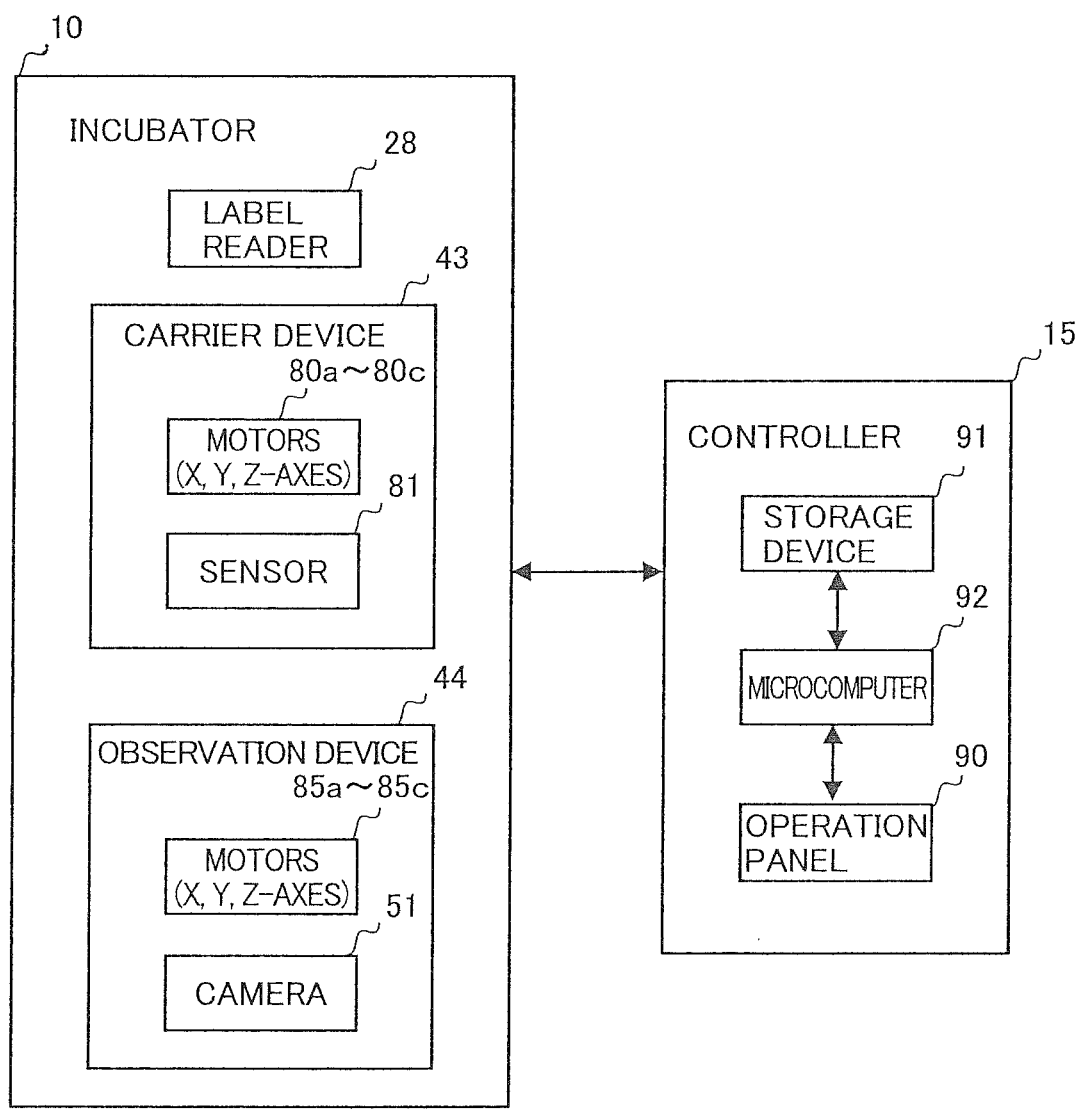
FIG. 17 illustrates an outline of the incubator 10 and a controller 15.

Here, description of the controller 15 for controlling the operation of the incubator 15 will be given with reference to FIG. 17. FIG. 17 illustrates the configurations of the incubator 10 and the controller 15, wherein only the principal blocks relevant to the control system of the incubator 10 are illustrated. Also, a detailed explanation of blocks that are in common with other drawings will be omitted appropriately.

The incubator 10 is provided with the label reader 28, the carrier device 43 and the observation device 44.

The carrier device 43 has an X-axis motor 80a for moving the slide plate 403 in the X-axis direction, a Y-axis motor 80b for moving the slide device 60 in the Y-axis direction, and a Z-axis motor 80c for moving the slider 405 in the Z-axis direction. The carrier device 43 also includes a sensor 81 for outputting positional information of the slide device 60 and the carrier table 62.

The observation device 44 is provided with motors 85a to 85c for moving the observation stand 50 in respective directions along the X-axis, Y-axis and Z-axis, and a camera 51.

The controller 15 is a device to integrally control the incubator 10 and is configured to include an operation panel 90, a storage device 91 and a microcomputer 92.

The operation panel 90 is a panel provided for a user to set the operating conditions of the isolator 10. A result from operating the operation panel 90 is transmitted to the microcomputer 92 and the controller 15 controls each block of the incubator 10 based on the result of the operation. Further, a result of the operation, status (e.g. temperature and humidity) of the incubator 10 and various kinds of information are displayed on the operation panel 90.

The storage device 91 stores program data to be executed by the microcomputer 92 and various kinds of data. The microcomputer 92 implements various kinds of functions by executing program data stored in the storage device 91.

Functional Blocks of the Microcomputer 92

Figure 18:
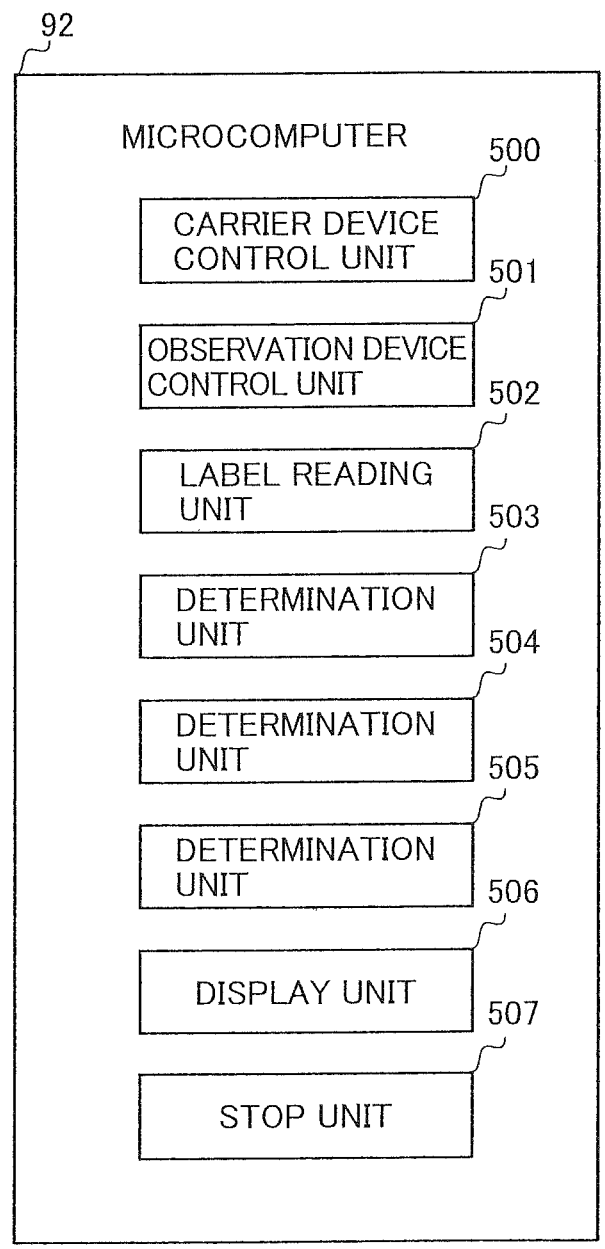
FIG. 18 illustrates functional blocks implemented by a microcomputer 92.

FIG. 18 illustrates functional blocks to be implemented by the microcomputer 92 by executing program data by the microcomputer 92. A carrier device control unit 500, an observation device control unit 501, label reading unit 502, determination units 503 to 505, a display unit 506 and a stop unit 507 are implemented by the microcomputer 92.

The carrier device control unit 500 controls the motors 80a to 80c based on a result from operation of the operation panel 90 (hereinafter referred to as the operation result) and an output of the sensor 81.

The observation device control unit 501 controls the camera 51 and the motors 85a to 85c based on the operational result.

The label reading unit 502 causes the label reader 28 to read a label affixed to a subject (i.e. the container 100 or the stacker 200).

The determination unit 503 determines whether a task (e.g. observation) under execution exists or not when an instruction to bring in or an instruction to take out is inputted as the operational result.

When the determination unit 503 determines that a task under execution exists, the determination unit 504 determines whether or not the task has been completed within a predetermined period of time.

The determination unit 505 determines whether or not all the containers stored in a designated stacker have been observed by the observation device 44.

The display unit 506 displays the operational result and the task under execution or other data on the operation panel 90.

The stop unit 507 stops the process which is being performed based on the currently inputted instruction (i.e. instruction to bring in or instruction to take out) when the determination unit 504 determines that the task under execution has not been completed within a predetermined period of time.

Example of the Bring in Process

Figure 19:
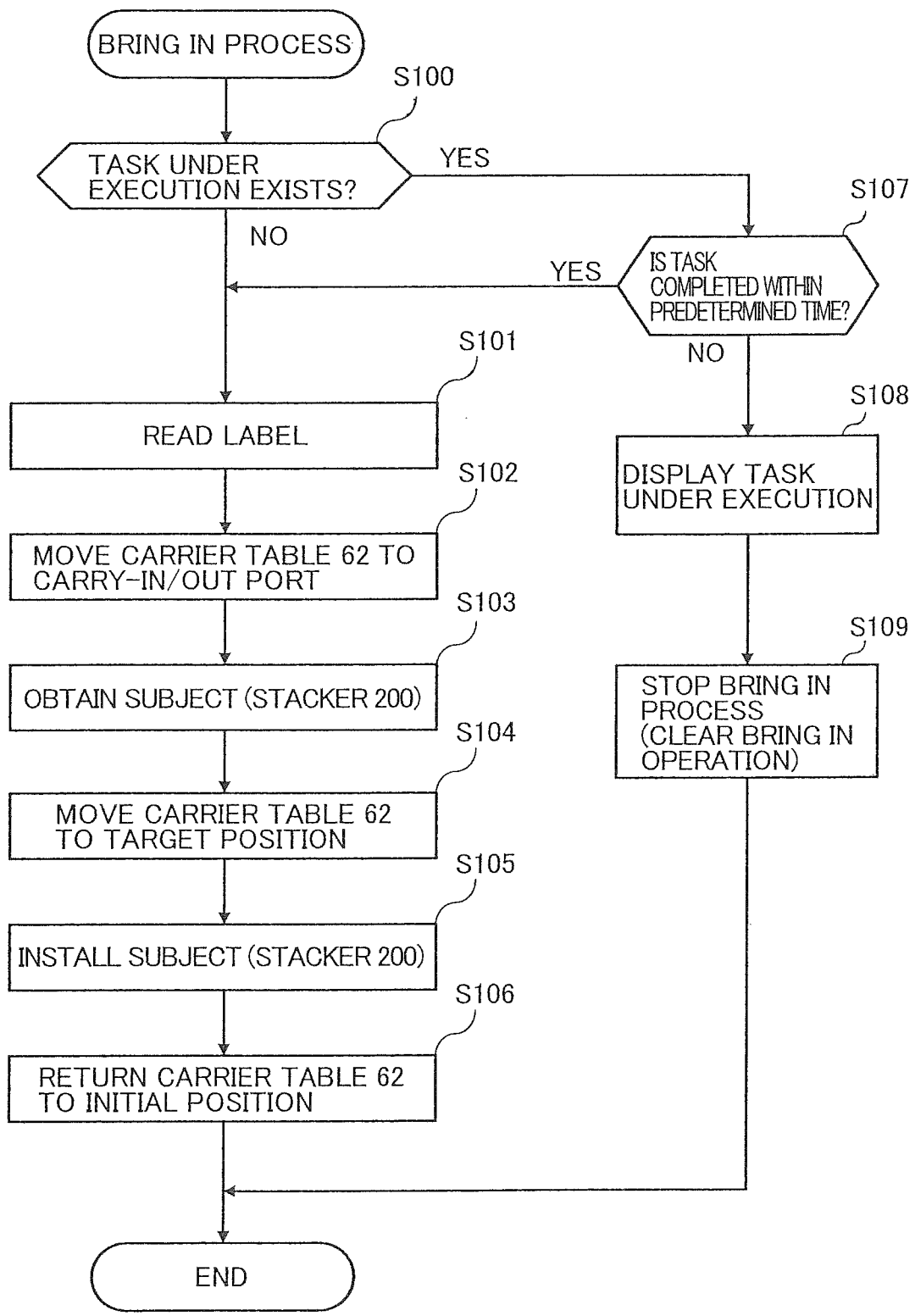
FIG. 19 is a flowchart illustrating an example of a process executed to bring in a subject.

FIG. 19 is a flowchart illustrating an example of a process executed when a subject (e.g. stacker 200) is brought in. Note that the controller 15 is assumed to open and close the carry-in/out door 27 appropriately. The process to bring in is also executed after the stacker 200 has been installed by a user on an installation stand (not shown) provided outside the culture chamber 22. It is assumed that the installation stand is arranged in a position allowing the label reader 28 read the label of a subject when the subject is installed. It is also assumed that the user has designated a destination to store the stacker 200 in accordance with the aforementioned sections.

Firstly, when an instruction to bring in is inputted via the operation panel 90, the determination unit 503 determines whether or not there exists a task under execution (S100). Then, when it is determined that no task is under execution (S100: NO), the label reading unit 502 causes the label reader 28 to read the label of the stacker 200 (S101). Note that the label reading unit 502 stores the information of the read label in the storage device 91. The carrier device control unit 500 moves the carrier table 62 to the carry-in/out port 26 (S102) and causes the carrier table 62 to obtain the stacker 200 (S103). Specifically, the carrier device control unit 500 moves the slide plate 403 so that the stacker 200 is loaded onto the slide plate 403. Then, the carrier device control unit 500 moves the carrier table 62 to the target position (S104) so that the stacker 200 is installed in the designated section (S105). The carrier device control unit 500 also returns the carrier table 62 to the designated initial position (S106).

Also, in process S100, when determining that a task under execution exists (S100: YES), the determination unit 504 determines whether or not the task under execution has been completed within a predetermined period of time (S107). Process S101 is executed when the task under execution has been completed within the predetermined period of time (S107: YES), whereas if process 101 has been executed but the task under execution has not been completed within the predetermined period of time (S107: NO), the display unit 506 displays the task under execution on the operation panel 90 (S108). Then, the stop unit 507 stops the bring in process based on an instruction to do so (S109).

By executing such processes, the stacker 200 which has been brought in is stored in a designated section of the culture chamber 22. In addition, in the present embodiment, the label reading unit 502 stores label information in the storage device 91 in relation with the section designated as the storage destination by the user.

Therefore, in the take out process, for example, the intended stacker 200 can be taken out by designating label information without designating the section.

Example of the Take Out Process

Figure 20:
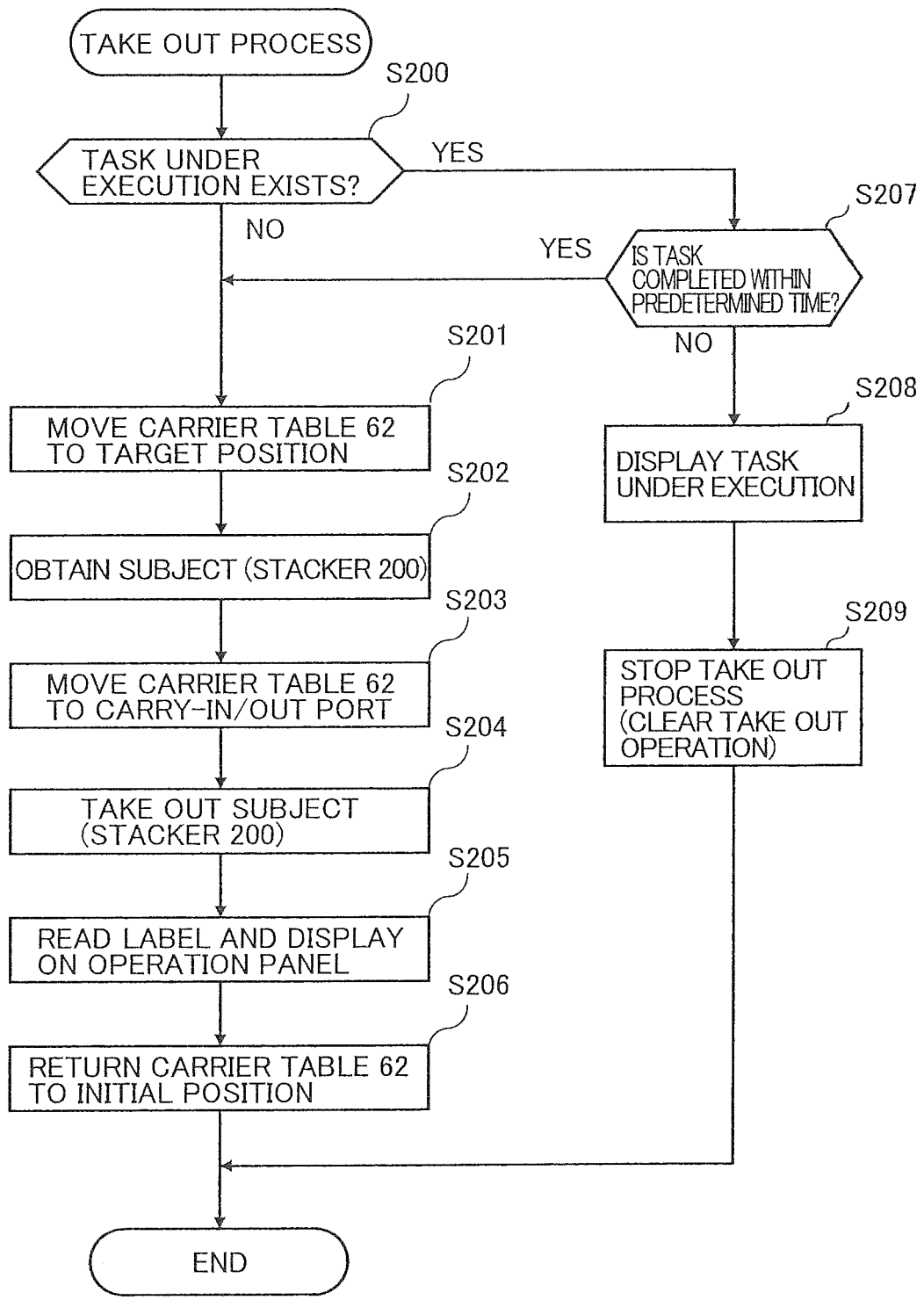
FIG. 20 is a flowchart illustrating an example of a process executed to take out a subject.

FIG. 20 is a flowchart illustrating a process executed when a subject (e.g. stacker 200) is taken out. Note that the controller 15 is assumed to open and close the carry-in/out door 27 appropriately. It is also assumed that a user designates, for example, the stacker 200 to be taken out based on label information. That is, the user inputs label information of the stacker 200 to be taken out via the operation panel 90.

Firstly, when an instruction to take out is inputted via the operation panel 90, the determination unit 503 determines whether or not there exists a task under execution (S200). Then, when it is determined that no task is under execution (S200: NO), the carrier device control unit 500 moves the carrier table 62 to a target position based on label information (S201). The carrier device control unit 500 also moves the carrier table 62 to obtain the stacker 200 with the designated label (S202). Then, the carrier device control unit 500 moves the carrier table 62 to the carry-in/out port 26 (S203) so that the stacker 200 is taken outside the culture chamber 22 (S204). The label reading unit 502 causes the label reader 28 to read the label of the stacker 200 and displays label information on the operation panel 90 (S205). As a result, the user can determine whether or not the stacker 200 with the designated label has been taken out. In addition, in process S205, the label reading unit 502 stores information of the read label in the storage device 91. Then, the carrier device control unit 500 returns the carrier table 62 to the designated initial position (S206).

Also, in process S200, when determining that a task under execution exists (S200: YES), the determination unit 504 determines whether or not the task under execution has been completed within a predetermined period of time (S207). Process S201 is executed when the task under execution has been completed within the predetermined period of time (S207: YES), whereas if process 201 has been executed but the task under execution has not been completed within the predetermined period of time (S207: NO), the display unit 506 displays the task under execution on the operation panel 90 (S208). Then, the stop unit 507 stops the take out process based on an instruction to do so (S209).

By executing such processes, the designated stacker 200 in the culture chamber 22 is taken out.

Example of Observation Process

Figure 21:
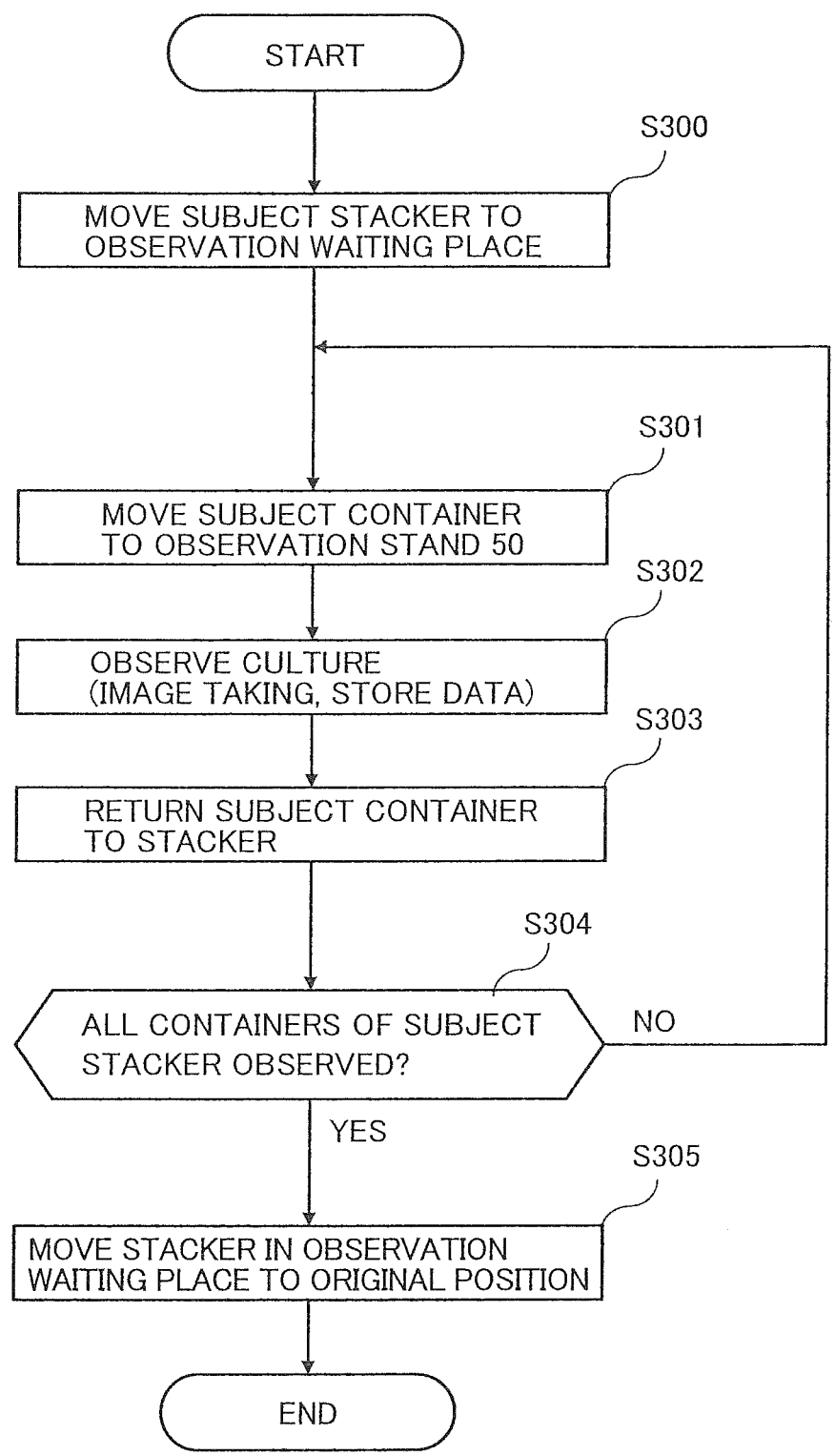
FIG. 21 is a flowchart illustrating an example of a process executed to observe a culture.

FIG. 21 is a flowchart illustrating an example of a process executed when a culture is observed. Here, a user operates the operation panel 90 to designate the stacker subjected to observation.

Firstly, when an instruction to start observation is inputted via the operation panel 90, the carrier device control unit 500 moves the designated subject stacker to section 7 which is the place to wait for observation (S300). Then, the carrier device control unit 500 moves the container subjected to observation from the subject stacker to the observation stand 50 of the observation device 44 (S301). Then, the observation device control unit 501 takes an image and/or a picture of the culture held in the subject container loaded on the observation stand 50 and stores data (i.e. image data and/or picture data) obtained by taking the picture, in the storage device 91 (S302). Thereafter, the carrier device control unit 500 returns the observed subject container to the stacker (S303). The determination unit 505 determines whether or not all the containers of the designated subject stacker have been observed (S304). If observation of all the containers of the subject stacker has been completed (S304: YES), the carrier device control unit 500 moves the stacker in section 7 serving as the observation waiting place to the original position (or original section) (S305). In contrast, if observation of all the containers of the subject stacker has not been completed (S304: NO), process S301 is executed again.

By executing such a process, all the cultures held in the containers stored in the designated stacker can be observed. And in this way, the containers subjected to observation are transported to a waiting place in units of stackers to carry/store individual containers (or trays) between the waiting place and the observation stand. Therefore, the carry distance can be kept at minimum to speedup and suppress effects on the subject of observation (i.e. culture) held in the container.

Note that in the observation process shown in FIG. 21, the observation process was executed immediately after inputting an instruction to start observation, however, the process is not limited to such. For example, process S100 shown in FIG. 19 or other processes may be executed. Further, the observation process of FIG. 21 may be executed after the microcomputer 92 determines whether or not the take out process has been executed, and temporarily suspends the take out process when the take out process has been executed, or the observation process may be executed after execution of the take out process.

In the foregoing description, the incubator 10 according to the present embodiment has been explained. In the carrier device 43, when the slide plate 403 on which the stacker 200 is loaded is moved to the predetermined position A, the guide mechanism 404 exerts a downward force on the stacker 200 which in turn is pressed against the slide plate 403. As a result, shaking of the stacker 200 when carried is suppressed effectively, whereby making it possible, for example, to prevent or suppress spilling and forming of waves by the culture solution. held in is the container stored in the stacker 200.

The present embodiment also provides a structure in which the stacker 200 having the tray 110 stored therein can be carried and the tray 110 holding the container can also be carried individually. Therefore, the structure is such that the tray 110 placed near the ceiling of the culture chamber 22 can be easily accessed by providing the guide receiving mechanism 310 in the carrier table 62, providing the guide mechanism 404 on the stacker 200 side and suppressing the vertical width of the carrier table 62.

Also, in the guide receiving mechanism. 310, the structure that presses against the stacker 200 is realized by utilizing elastic force of common springs 352a and 352b. Accordingly, the present embodiment makes it possible to prevent sway of the stacker 200 by using inexpensive components.

The slide plate 403 also has a shape that allows selective loading of the stacker 200 or the tray 110 storing the container 100. Therefore, the carrier device 43 in the present embodiment can carry a subject selected from the container 100 and the stacker 200.

The slide plate 403 also has a protruding part (i.e. position determination means) to determine the position of the tray 110 and the stacker 200 and restrict movement thereof in the horizontal direction. Therefore, the carrier device 43 can carry not only the tray 110 but also the stacker 200 in a stable manner.

For example, as opposed to the present embodiment, the guide mechanism 404 may be mounted on the stacker 200 and the guide receiving mechanism 310 may be mounted on the carrier table 62. Even in such a case, effects similar to those of the present embodiment can be obtained.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. A carrier device comprising:
a loading board;
a moving mechanism configured to move the loading board in a horizontal direction so that a storage member and a tray are loaded on the loading board, the storage member being configured to store a plurality of containers for storing liquid, the containers each fitting into the tray;
a base material configured to have set thereon the loading board and the moving mechanism;
a first mounting member mounted to the base material, the first mounting member including a guide member and guide rollers; and
a carrier mechanism configured to carry the base material so as to carry the storage member to a target position after the loading board is moved to the predetermined position, wherein
a second mounting member is mounted on a side face of the storage member, the second mounting member including a guide rail and a bulged member,
the first mounting member is provided in a position corresponding to the guide rail,
the guide rail has an aperture arranged on a bottom side thereof,
the bulged member is inserted into the aperture from the bottom side and is mounted on the guide rail by a bolt whose shaft portion is inserted into a spring,
the guide rollers are mounted to the guide member,
the guide rail is horizontally movable along the guide member, and
when the guide rollers ride on the bulged member, in association with a horizontal movement of the guide rail, the guide rollers exert a downward force on the storage member, and the first mounting member pushes the second mounting member mounted on the storage member to press the storage member against the loading board.

2. The carrier device according to claim 1, wherein
the loading board has protruding parts formed on an upper surface thereof,
the storage member and the tray have apertures or recesses,
the storage member and the tray are loaded on the loading board in a state where the protruding parts fit into the apertures or recesses.

3. A culture apparatus comprising:
a culture chamber configured to cultivate a culture;
a carry-in/out port provided to a wall of the culture chamber;
a door configured to open or close the carry-in/out port;
a storage rack having a plurality of sections configured to store a storage member for storing a container to contain the culture, the container fitting into a tray; and
a carrier device configured to carry the storage member and/or the container through the carry-in/out port,
the carrier device including
a loading board,
a moving mechanism configured to move the loading board in a horizontal direction so that the storage member and the tray are loaded on the loading board,
a base material configured to have set thereon the loading board and the moving mechanism,
a first mounting member mounted to the base material, the first mounting member including a guide member and guide rollers, and
a carrier mechanism configured to carry the base material so as to carry the storage member to a target position after the loading board is moved to the predetermined position, wherein
a second mounting member is mounted on a side face of the storage member, the second mounting member including a guide rail and a bulged member,
the first mounting member is provided in a position to correspond to the guide rail,
the guide rail has an aperture arranged on a bottom side thereof,
the bulged member is inserted into the aperture from the bottom side and is mounted on the guide rail by a bolt whose shaft portion is inserted into a spring,
the guide rollers are mounted to the guide member,
the guide rail is horizontally movable along the guide member, and
when the guide rollers ride on the bulged member, in association with a horizontal movement of the guide rail, the guide rollers exert a downward force on the storage member, and the first mounting member pushes the second mounting member mounted on the storage member to press the storage member against the loading board.

4. The culture apparatus according to claim 3, wherein
the loading board has protruding parts formed on an upper surface thereof, the storage member and the tray have apertures or recesses, the storage member and the tray are loaded on the loading board in a state where the protruding parts fit into the apertures or recesses.

5. A culture apparatus, comprising:

a culture chamber configured to cultivate a culture;

a carry-in/out port provided to a wall of the culture chamber;

a door configured to open or close the carry-in/out port;

a storage rack having a plurality of sections configured to store a storage member for storing a container to contain the culture, the container fitting into a tray; and a carrier device configured to carry the storage member and/or the container through the carry-in/out port, the carrier device including a loading board, a moving mechanism configured to move the loading board in a horizontal direction so that the storage member and the tray are loaded on the loading board, a base material configured to have set thereon the loading board and the moving mechanism, a first mounting member mounted to the base material, the first mounting member including a guide member and guide rollers, and a carrier mechanism configured to carry the base material so as to carry the storage member to a target position after the loading board is moved to the predetermined position, wherein a second mounting member is mounted on a side face of the storage member, the second mounting member including a guide rail and a bulged member, the first mounting member is provided in a position to correspond to the guide rail, the guide rail has an aperture arranged on a bottom side thereof, the bulged member is inserted into the aperture from the bottom side and is mounted on the guide rail by a bolt whose shaft portion is inserted into a spring, the guide rollers are mounted to the guide member, the guide rail is horizontally movable along the guide member, when the guide rollers ride on the bulged member, in association with a horizontal movement of the guide rail, the guide rollers exert a downward force on the storage member, and the first mounting member pushes the second mounting member mounted on the storage member to press the storage member against the loading board, an observation device to observe a culture stored in the container of at least one of the sections is included and a section in the vicinity of the observation device is set as an observation waiting place, and the storage member accommodating a container subjected to observation is transported to the observation waiting place by the carrier mechanism and a container stored in a storage member placed in the observation waiting place is carried to the observation device for observation.

6. The culture apparatus according to claim 5, wherein the loading board has protruding parts formed on an upper surface thereof, the storage member and the tray have apertures or recesses, the storage member and the tray are loaded on the loading board in a state where the protruding parts fit into the apertures or recesses.

\* \* \* \* \*